(12) United States Patent
Meter

(10) Patent No.: US 11,486,870 B2
(45) Date of Patent: Nov. 1, 2022

(54) METHOD FOR DETERMINING THE GENDER OF A CHICKEN EMBRYO

(71) Applicant: SELEGGT GmbH, Cologne (DE)

(72) Inventor: Tjitze Meter, Rhenen (NL)

(73) Assignee: SELEGGT GmbH, Cologne (DE)

( * ) Notice: Subject to any disclaimer, the term of this patent is extended or adjusted under 35 U.S.C. 154(b) by 164 days.

(21) Appl. No.: 17/053,075

(22) PCT Filed: May 28, 2019

(86) PCT No.: PCT/EP2019/063870
§ 371 (c)(1),
(2) Date: Nov. 5, 2020

(87) PCT Pub. No.: WO2019/229084
PCT Pub. Date: Dec. 5, 2019

(65) Prior Publication Data
US 2021/0072211 A1 Mar. 11, 2021

(30) Foreign Application Priority Data
May 30, 2018 (NL) .................... 2021022

(51) Int. Cl.
*A01K 43/00* (2006.01)
*G01N 33/08* (2006.01)
*G01N 21/84* (2006.01)

(52) U.S. Cl.
CPC ........... *G01N 33/085* (2013.01); *A01K 43/00* (2013.01); *G01N 21/84* (2013.01)

(58) Field of Classification Search
CPC ...... G01N 33/085; G01N 21/84; G01N 33/08; A01K 43/00

USPC ......................................... 356/53
See application file for complete search history.

(56) References Cited

U.S. PATENT DOCUMENTS

2012/0318981 A1 12/2012 Steiner et al.
2017/0205353 A1 7/2017 Galli et al.

FOREIGN PATENT DOCUMENTS

| CA | 2991603 A1 | 2/2017 |
| DE | 102007013107 A1 | 9/2008 |
| DE | 102016013155 A1 | 4/2018 |
| WO | 2017174337 A1 | 10/2017 |

OTHER PUBLICATIONS

Galli et al.: "In ovo sexing of chicken eggs by fluorescence spectroscopy", Analytical and Bioanalytical Chemistry, Springer, DE, vol. 409, No. 5, Dec. 14, 2016 (Dec. 14, 2016), pp. 1185-1194, XP036142794, ISSN: 1618-2642, DOI: 10.1007/S00216-016-0116-6 [retrieved on Dec. 14, 2016].

*Primary Examiner* — Md M Rahman
(74) *Attorney, Agent, or Firm* — N.V. Nederlandsch Octroolbureau

(57) ABSTRACT

The present invention relates to a method for spectroscopical in-ovo gender determination of fertilized and incubated bird eggs comprising the steps of:
a. providing a number of passages in an egg shell of an egg for allowing entrance into an interior of the egg and/or exit from the interior of the egg of electromagnetic waves suitable for spectroscopy,
b. introducing electromagnetic waves into the interior of the egg
c. detecting electromagnetic waves exiting the egg;
d. analysing, by spectroscopy, of the exiting electromagnetic waves at at least one passage of the number of passages; and
e. determining the gender of a chicken embryo.

10 Claims, 3 Drawing Sheets

METHOD FOR DETERMINING THE GENDER OF A CHICKEN EMBRYO

FIELD OF THE INVENTION

Figure 1:
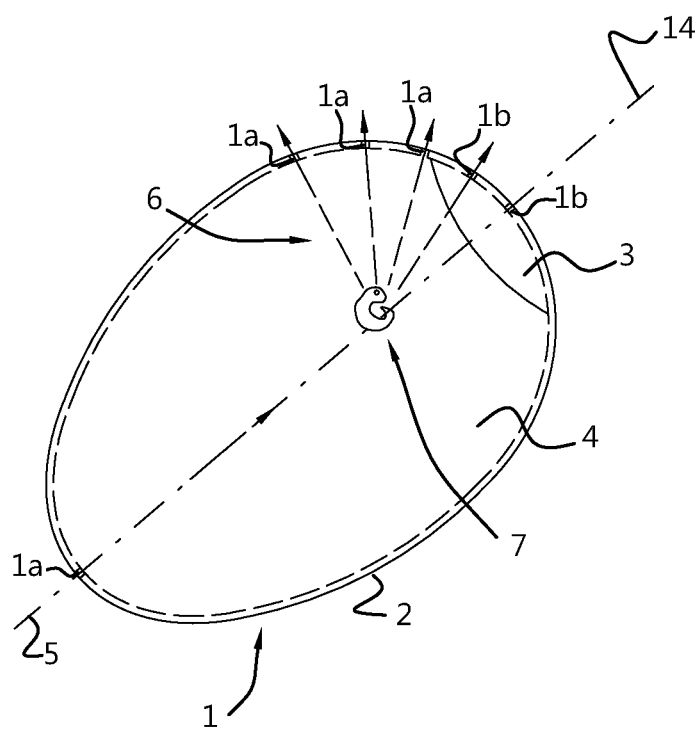

The present invention relates to a method for spectroscopical in-ovo gender determination of fertilized and incubated bird eggs comprising the step of introducing electromagnetic waves into the interior of the egg. More generally, the present invention relates to a method for spectroscopical analyses of fertilized and incubated bird eggs.

BACKGROUND ART

It is known to use spectroscopy to determine the gender of chicken embryo's. For example CA2991603 relates to a method and a device for introducing an opening into the calcareous shell of incubated bird eggs, having embryos contained therein, in the region of the blunt end of the incubated eggs. Within the region of the blunt end, there is an outer membrane and an inner membrane, between which there is an air chamber. The device has a retaining device, on which the incubated bird eggs are placed with the pointed end facing downwards, wherein the embryo is positioned adjacent to the inner membrane; a first detection device to determine the position and geometry of the air chamber; and an opening device to introduce an opening into the calcareous shell at the blunt end of the incubated bird egg above the tensioned inner membrane. As a result of the opened calcareous shell, a sex determination of the embryo can be reliably carried out. With the help of the opening it is possible to determine the sex of the embryo non-invasively, e.g., with the help of spectroscopic methods such as Raman spectroscopy and/or fluorescence spectroscopy. The bird eggs need to be closed again after the sex has been determined. Thus, further development of the embryo is ensured.

Also, WO 2017/174337 relates to a method and to a device for optical in ovo sex determination of fertilized and incubated birds' eggs having the following steps: monitoring the time progression of the incubation until a detectable blood vessel is formed, making a hole in the calcium carbonate shell of the bird's egg, searching for the blood vessel forming in the egg by means of a vision system, positioning the blood vessel, irradiating the blood vessel with a laser beam source emitting an excitation wavelength, registering the backscatter radiation of the irradiated blood vessel by means of a detector which is connected to an evaluation unit. These are followed by the steps of evaluating the backscatter radiation including the fluorescent radiation in the evaluation unit from the registered spectral intensity of the fluorescent radiation in a spectral range red-shifted to the excitation wavelength, wherein the sex-specific characteristics of the male blood and of the female blood are contained in the intensity and in the spectral profile of the registered fluorescent radiation and wherein at least one of the intensity values determined from the measured spectral intensities of the fluorescent radiation intensity with respect to the male blood have an evaluatable different value by comparison with at least one of the determined intensity values with respect to the female blood in the blood vessels, determining the sex of the bird's egg from the difference of at least one of the values of the fluorescent intensity values in the evaluation unit and then at least displaying the sex of the embryo in the bird's egg determined in the evaluation unit.

The known methods of optical in ovo gender determination involve too much risk for the embryo, in particular in an industrial environment, because the known method require large openings in the egg shell.

SUMMARY OF THE INVENTION

The present invention seeks to provide a method for producing chicken wherein the determining the gender of chicken embryo's is more reliable, and suitable for application on industrial scale, and involves less risk for the embryo.

In addition, the present invention seeks to provide a method for producing chicken including the determining the gender of chicken embryo's, wherein a problem with known methods is at least partly solved.

Moreover, the present invention seeks to provide an alternative method for producing chicken including the determining the gender of chicken embryo's.

Therefore, the invention provides a method for spectroscopical in-ovo gender determination of fertilized and incubated bird eggs comprising the steps of:

a. providing a number of passages in an egg shell of an egg for allowing entrance into an interior of the egg and/or exit from the interior of the egg of electromagnetic waves suitable for spectroscopy, b. introducing electromagnetic waves into the interior of the egg c. detecting electromagnetic waves exiting the egg;

d. analysing, by spectroscopy, of the exiting electromagnetic waves at at least one passage of the number of passages; and e. determining the gender of a chicken embryo based on step d).

Providing a number of passages in an egg shell of an egg for allowing entrance into an interior of the egg and/or exit from the interior of the egg of electromagnetic waves enables to distribute the required amount of electromagnetic waves between more passages. Therefore, the passages can be smaller and damage and harm to the egg and embryo is limited which is crucial for a delicate fertilized egg in an industrial environment.

In an embodiment, the spectroscopy is laser spectroscopy. Although, every wave suitable for spectroscopy is conceivable, use of a laser for spectroscopy has well known benefits.

In an embodiment of the method, step a) comprises providing passages at opposite sides of the egg. Providing passages at opposite sides of the egg enables to increase the interaction between the embryo and/or blood vessel in the interior of the egg and the electromagnetic waves. This is in particular relevant in case of transmission- and absorption-spectroscopy.

In an embodiment of the method, step a) comprises providing passages at a height of an embryo situated in the egg. Providing passages at the height of an embryo situated in the egg even more increases the interaction between the embryo in the interior of the egg and the electromagnetic waves.

In an embodiment of the method, step a) is performed using laser processing, and at least one passage of the number of passages has a dimension between 0.01 mm to 0.5 mm, in particular between 0.01 mm to 0.05 mm. These small passages have also benefits in connection with scattering. The laser processing is in particular suitable to make a small passage in the egg shell. The dimension is generally a diameter of the passage. The small diameter of the passage also enables to use self-closing capabilities of the egg with respect to the passage, so that risk to harm the embryo is reduced further. The passage may have a cylindrical shape, however a tapered shape is conceivable as well.

In an embodiment of the method, an outer calcareous shell is removed by the laser processing to provide at least one passage of the number of passages while an egg membrane adjacent the calcareous shell is maintained. This passage facilitates entrance of the electromagnetic waves into the interior of the egg but however still closes off the interior of the egg by the inner membrane. Therefore, risk to harm the embryo is reduced even further.

In an embodiment of the method, step c) comprises detecting electromagnetic waves exiting the egg at at least two passages of the number of passages. This increases the amount of detected electromagnetic waves while avoiding the need of a big opening that is normally required for that amount. It will be understood that the detected electromagnetic waves are used as input for the spectroscopy.

In an embodiment of the method, step c) comprises individually detecting electromagnetic waves exiting the egg at each of the at least two passages of the number of passages. Individually detecting at each of the two, or even all, passages enables to build in a redundancy and improve the detection.

In an embodiment, the method further comprises providing the number of passages with a pattern that defines their spatial distribution over the egg shell.

Therefore, the invention provides a test device configured to perform the method of any preceding claim.

Therefore, the invention provides a method for spectroscopical in-ovo analyses of fertilized and incubated bird eggs comprising the steps of:
    forming a passage in an egg shell of an egg,
    detecting a blood vessel in an interior of the egg,
    providing a passage in the blood vessel,
    expelling an amount of blood from the blood vessel;
    subjecting the amount of blood to spectroscopy.

Performing spectroscopy directly on the amount of blood reduces the required amount of electromagnetic waves and therefore, the passages can be even smaller and damage and harm to the egg and embryo is limited which is crucial for a delicate fertilized egg in an industrial environment.

The passage is formed or provided in a blood vessel that is part of, or highly integrated with, a membrane in the interior of the egg, more precise, the chorioallantoic membrane.

In an embodiment of the method, providing a passage in the blood vessel is performed by laser cutting the blood vessel through the passage in the egg shell. This enables to use laser processing for both forming a passage in the egg shell and the passage in the blood vessel.

In an embodiment of the method, the steps of
    expelling an amount of blood from the blood vessel; and
    subjecting the amount of blood to spectroscopy
are performed in the interior of the egg. This facilitates subjecting the blood more directly to spectroscopy. Performed in the interior of the egg means that at least the interaction between the amount of blood and the electromagnetic waves used for the spectroscopy is in the interior of the egg.

In an embodiment, the method comprises
    wherein expelling an amount of blood from the blood vessel comprises expelling an amount of blood from the blood vessel to an exterior of the egg; and
    wherein subjecting the amount of blood to spectroscopy comprises subjecting the amount of blood to spectroscopy at the exterior of the egg. This even more facilitates subjecting the blood more directly to spectroscopy.

Although, the amount of blood is analysed "ex ovo", the method can still be considered an "in ovo" method because the embryo is still "in ovo".

In an embodiment of the method, the expelling the amount of blood from the blood vessel and through the passage to an exterior of the egg comprises;
    fluid coupling an interior of the egg to a source of pressure,
    controlling the pressure in the interior of the egg by the source of pressure,
    expelling the amount of blood from the interior of the egg to the exterior of the egg as a result of the pressure in the interior of the egg. This facilitates the expelling the amount of blood to the exterior of the egg.

In an embodiment of the method, the spectroscopy comprises laser spectroscopy. Although, every wave suitable for spectroscopy is conceivable, use of a laser for spectroscopy has well known benefits.

In an embodiment of the method, the analyses comprises gender determination of fertilized and incubated bird eggs.

SHORT DESCRIPTION OF DRAWINGS

Figure 2:
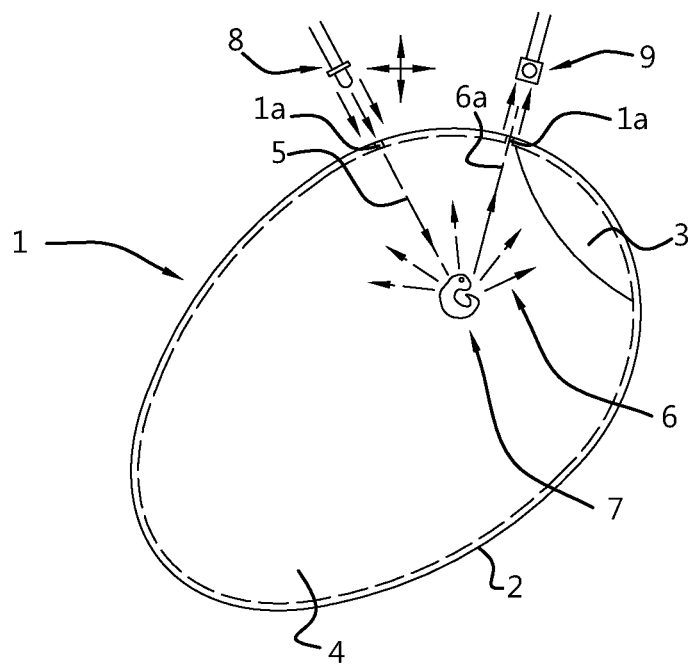
Figure 3A:
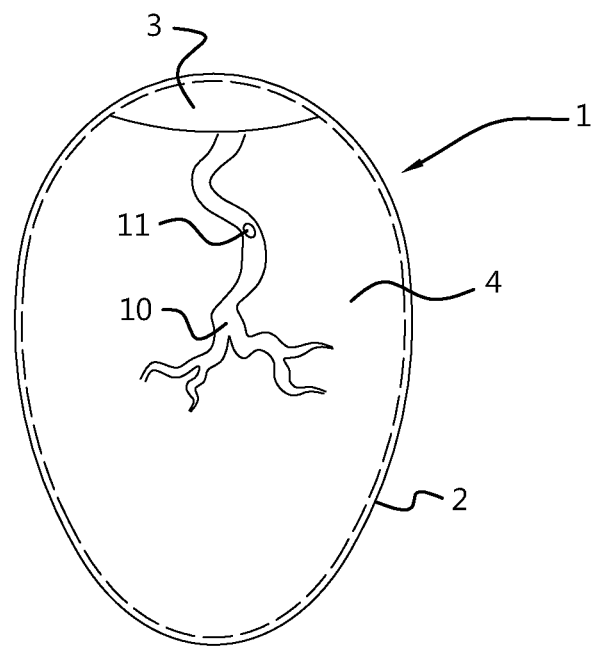
Figure 3B:
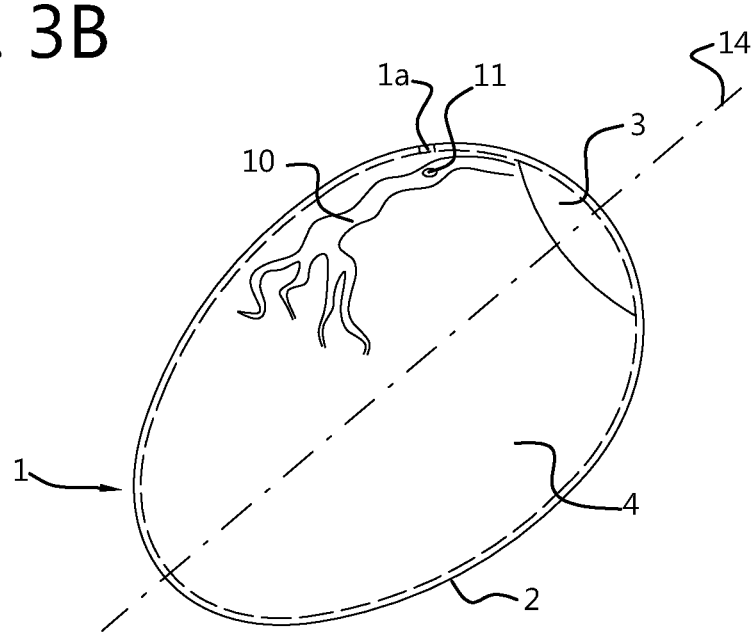
Figure 3C:
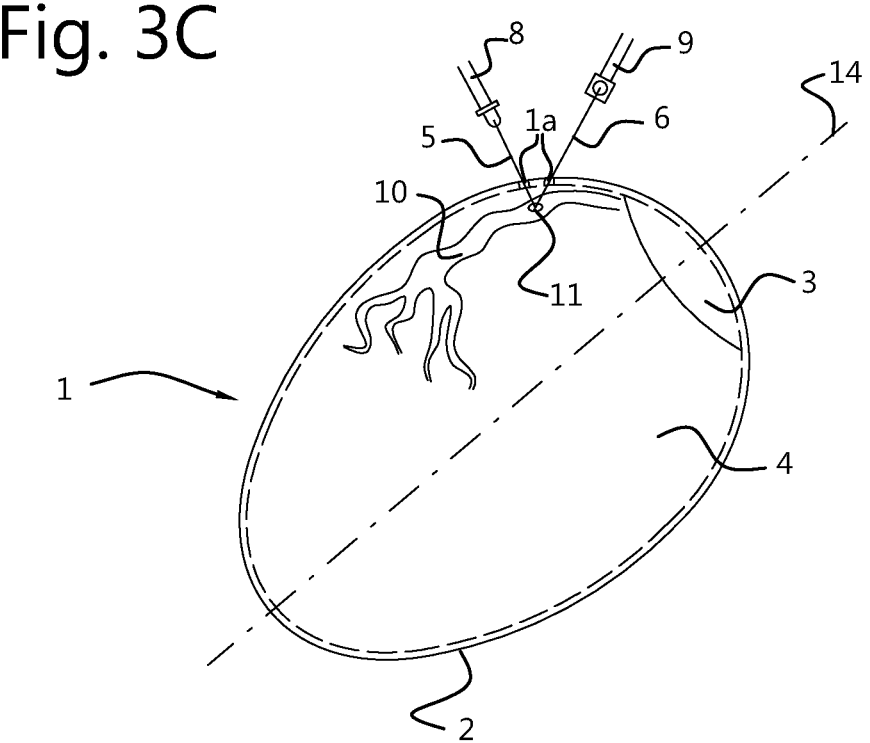
Figure 4:
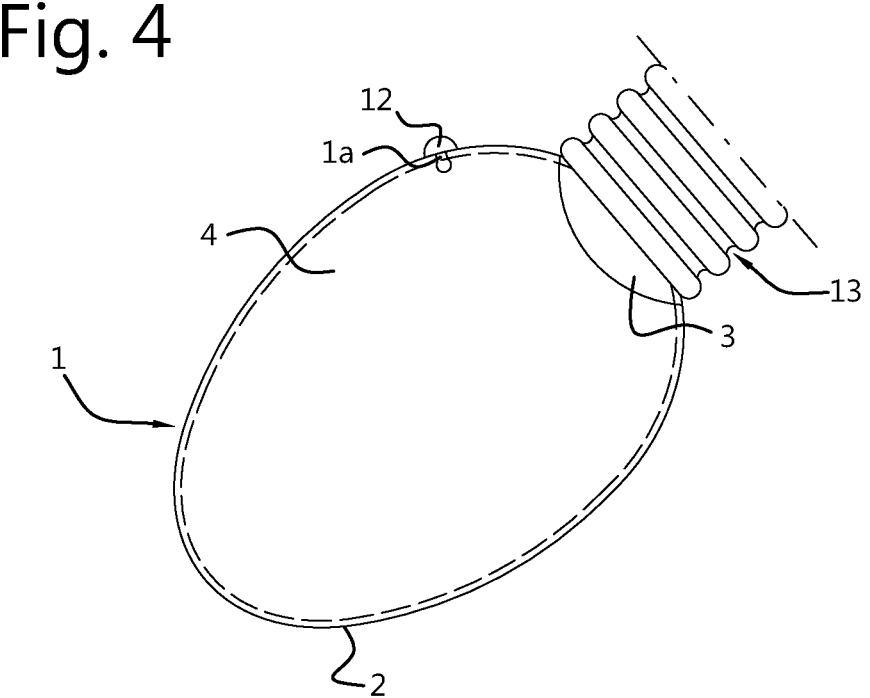

The present invention will be discussed in more detail below, with reference to the attached drawings, in which
    FIG. 1 is a side view in cross section of an egg subjected to the method according to the invention;
    FIG. 2 is a side view in cross section of an egg subjected to another embodiment of the method according to the invention,
    FIG. 3A-C show different side views in cross section of an egg subjected to another method according to the invention,
    FIG. 4 is a side view in cross section of an egg subjected to another embodiment of the method of FIG. 3A-C.

DESCRIPTION OF EMBODIMENTS

FIG. 1 is a side view in cross section of an egg 1 subjected to the method according to the invention. The bird egg 1 is fertilized and incubated for a certain period of time. The egg 1 therefore holds a chicken embryo 7 in a certain degree of development. In order to determine the gender of the chicken embryo 7, the egg 1 is subjected to a method for spectroscopical in-ovo gender determination of fertilized and incubated bird eggs.

The method comprises the step providing a number of passages 1a, 1b in an egg shell 2 of the egg 1. The providing or forming of such a passage 1a, 1b is performed using laser processing. Therefore, the passage 1a, 1b can have a small diameter between 0.01 mm to 0.5 mm, in particular between 0.01 mm to 0.05 mm. The passages 1a, 1b allow entrance of electromagnetic waves in the form of a laser beam into an interior 4 of the egg 1 as well as exit from the interior 4 of the egg 1. The holes 1b open in the so called air cell 3 of the egg 1. The holes 1a open into the main interior 4 of the egg 1 where the embryo 7 is situated. The egg comprises passages 1a, 1b at opposite sides of the egg 1. In this case, the egg 1 comprises passages 1a, 1b at opposite sides of the egg 1 at central axis 14 of the egg 1.

The egg comprises passages 1a, 1b at the height of the embryo 7 situated in the egg 1. Here, these passages 1a, 1b are provided at the blunt side of the egg 1. The passages 1a, 1b are provided according to a pattern that defines their spatial distribution over the egg shell.

The method comprises the step of introducing the laser beam into the interior 4 of the egg 1 through, here one, hole 1a. The laser beam 5 introduced into the interior 4 interacts with the embryo 7. The interaction between the laser beam and the embryo 7 results in a detectable characteristic. The interaction may involve any of transmission, absorption, reflection or any other suitable interaction. The detectable characteristic is determined by spectroscopy on the laser beam exiting the interior 4 of the egg 1 at holes 1a, 1b. In this case, the laser beam 6 exits at a number of holes 1a, 1b. The laser beam 6 can be individually detected at two or more passages. Alternatively, a joint detector can be used to detect the laser beams that exit the passages 1a, 1b. Analyzing of light, here laser light, by spectroscopy is known per se and therefore not described in this application. Based on the determined characteristic, the gender of the chicken embryo 7 is determined. The determination involves comparing a characteristic with a known reference response to laser light of an embryo with a defined gender in order to determine the gender of the chicken embryo 7.

FIG. 2 is a side view in cross section of an egg 1 subjected to another embodiment of the method according to the invention. Difference with the embodiment of FIG. 1 are described. The egg 1 has one passages 1a that allows entrance of electromagnetic waves in the form of a laser beam into an interior 4 of the egg 1. The egg 1 has another passages 1a that allows exit of electromagnetic waves in the form of a laser beam from the interior 4 of the egg 1. A laser source 8 emits the laser beam 5 through the passage 1a into the interior 4 of the egg 1. A detector 9 receives the laser beam 6a that exits the passage 1a to provide data for spectroscopic analyses. Here, the detector 9 individually detects electromagnetic waves exiting the egg at the single passages 1a.

FIG. 3A-C show different side views in cross section of an egg 1 subjected to another method according to the invention.

The bird egg 1 is fertilized and incubated for a certain period of time. The egg 1 therefore holds a chicken embryo, that is not shown here, in a certain degree of development. In order to analyse the chicken embryo 7, the egg 1 is subjected to a method for spectroscopical in-ovo analyses that may include gender determination of fertilized and incubated bird eggs. The method for spectroscopical in-ovo analyses of fertilized and incubated bird eggs comprising the step of providing a passage 1a in the egg shell of the egg 1. A blood vessel 10 is detected in the interior 4 of the egg 1. The blood vessel 10 is shown very schematically for illustration purposes. In reality, the blood vessel 10 is part of, or highly integrated with a membrane in the interior 4 of the egg 1. The membrane, that is generally referred to as "chorioallantoic membrane" is not shown here. The blood vessel 10 can be detected by any suitable means, like an imaging means. After the blood vessel 10 is detected, a passage 11 is formed or provided. Here, the passage 11 in the blood vessel 10 is formed by laser cutting the blood vessel through the passage 1a in the egg shell 2. After the passage 11 in the blood vessel 10 is formed, an amount of blood is expelled from the blood vessel. Therefore, the blood is more freely accessible to analyses like spectroscopy.

Here, the amount of blood is subjected to spectroscopy, in this case laser spectroscopy, in the interior 4 of the egg 1 as shown in FIG. 3C and described in connection with 2. Therefore, the amount of blood is expelled from the blood vessel 11 into the interior 4 of the egg 1 and then the amount of blood is subjected to spectroscopy in the interior 4 of the egg 1. In other words, both steps of in short expelling and spectroscopy are performed in the interior 4 of the egg 1.

FIG. 4 is a side view in cross section of an egg 1 subjected to another embodiment of the method of FIG. 3A-C, that is the method for spectroscopical in-ovo analyses determination of fertilized and incubated bird eggs 1. The analyses may comprise gender determination of fertilized and incubated bird eggs 1. The method comprises expelling an amount of blood from the blood vessel 10 shown in FIG. 3C, to an exterior of the egg 1. After expelling the amount of blood 12 from the blood vessel 10 shown in FIG. 3C, to an exterior of the egg 1, the amount of blood 12 is subjected to spectroscopy at the exterior of the egg 1. Here, the expelling of the amount of blood 12 from the blood vessel and through the passage 1a to an exterior of the egg 1 comprises fluid coupling an interior 4 of the egg 1 to a source of pressure. The source of pressure is a pressure cup 13 that is connected at the blunt side of the egg where the air cell 3 of the egg 1 is situated. The shell 2 of the egg 1 is permeable at the air cell 3 and therefore controlling the pressure in the interior 4 of the egg 1 by the source of pressure is possible. The expelling the amount of blood 12 from the interior 4 of the egg 1 to the exterior of the egg 1 is facilitated as a result of the controlled pressure in the interior 4 of the egg 1.

The invention claimed is:

1. A method for spectroscopical in-ovo gender determination of fertilized and incubated bird eggs comprising the steps of:
   a. providing a number of passages in an egg shell of an egg for allowing entrance into an interior (d) of the egg and/or exit from the interior of the egg of electromagnetic waves suitable for spectroscopy,
   b. introducing electromagnetic waves into the interior of the egg,
   c. detecting electromagnetic waves exiting the egg,
   d. analyzing by spectroscopy of the exiting electromagnetic waves at least one passage of the number of passages; and
   e. determining the gender of a chicken embryo (7) based on step d).

2. The method according to claim 1, wherein the spectroscopy is laser spectroscopy.

3. The method according to claim 1, wherein step a) comprises providing passages at opposite sides of the egg.

4. The method according to claim 1, wherein step a) comprises providing passages at a height of an embryo situated in the egg.

5. The method according to claim 1, wherein step a) is performed using laser processing, and at least one passage of the number of passages has a dimension between 0.01 mm to 0.5 mm, in particular between 0.01 mm to 0.05 mm.

6. The method according to claim 5, wherein an outer calcareous shell is removed by the laser processing to provide at least one passage of the number of passages while an egg membrane adjacent the calcareous shell is maintained.

7. The method according to claim 1, wherein step c) comprises detecting electromagnetic waves exiting the egg at at least two passages of the number of passages.

8. The method according to claim 7, wherein step c) comprises individually detecting electromagnetic waves exiting the egg at each of the at least two passages of the number of passages.

9. The method according to claim 1, and further comprising providing the number of passages with a pattern that defines their spatial distribution over the egg shell.

10. Test device configured to perform the method of claim 1.

* * * * *